United States Patent [19]

Ueno

[11] Patent Number: 4,682,644
[45] Date of Patent: Jul. 28, 1987

[54] MOLD FOR USE IN DENTAL PRECISION CASTING

[75] Inventor: Masato Ueno, Hiroshima, Japan

[73] Assignee: Kyocera Kabushiki Kaisha, Kyoto, Japan

[21] Appl. No.: 558,496

[22] Filed: Dec. 6, 1983

[30] Foreign Application Priority Data

Dec. 6, 1982 [JP] Japan .................................. 57-214372
Jun. 28, 1983 [JP] Japan .................................. 58-117723

[51] Int. Cl.⁴ .......................... B22C 9/04; B22C 9/08
[52] U.S. Cl. .................................. 164/359; 164/361; 164/376; 249/54; 249/62
[58] Field of Search .............. 164/359, 361, 360, 376, 164/286, 122, 123, 125, DIG. 4, DIG. 15; 249/54, 62, 106, 111, 137

[56] References Cited

U.S. PATENT DOCUMENTS 2,569,899 10/1951 Miner .................................. 164/359
3,480,070 11/1969 Beetle et al. .................... 164/359 X
3,815,665 6/1974 Baur .................................... 164/359

FOREIGN PATENT DOCUMENTS 1193648 5/1965 Fed. Rep. of Germany ...... 249/197
186656 11/1966 U.S.S.R. .............................. 164/359

*Primary Examiner*—J. Reed Batten, Jr.
*Attorney, Agent, or Firm*—Spensley Horn Jubas & Lubitz

[57] ABSTRACT

In casting metals for dental prosthetic use, superior dental castings free from shrinkage cavities can be obtained by delaying the cooling and solidification of molten metal in mold members such as a sprue, runner and gate and, if necessary, a molten metal reservoir into which the molten metal is poured. Such delay in cooling and solidification can be achieved either by forming the sprue and the like from a heat resisting ceramic tubular body or by further forming a heat insulating layer on the outer periphery of the tubular body.

31 Claims, 18 Drawing Figures

FIG. 14    FIG. 15    FIG. 16
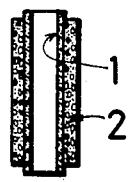 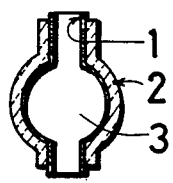 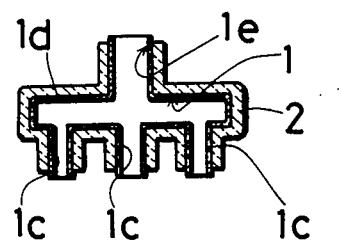
FIG. 17    FIG. 18
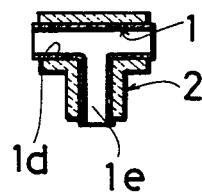 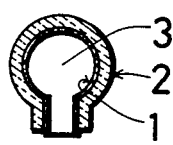

MOLD FOR USE IN DENTAL PRECISION CASTING

BACKGROUND OF THE INVENTION

1. Field of the Invention.

This invention relates to a mold member used in the precision casting of metals for dental prosthetic use and capable of delaying and preventing the solidification of the molten metal staying in the mold member called a sprue, runner, gate and molten metal reservoir adapted for feeding the metal into the mold cavity before the casting cools and solidifies.

2. Prior Art

It was a general practice to employ a lost-wax process in the conventional precision casting of dental metals (either centrifugal casting or pressure casting, in which the former is used in the description of the invention that follows) because of the smallness of the articles to be cast.

According to the lost-wax process, recourse is had to centrifugal casting which is carried out in such a manner that a casting and a sprue, runner, gate and, if necessary, a molten metal reservoir are produced from wax, the mold members thus produced are set in a ring filled with an investment compound, thereafter are heated at temperatures of 800° to 900° C. to burn the wax to make hollow the members corresponding to the wax, and molten metal for a casting such as a nickelchromium alloy (meltable at 1200°–1300° C.) is poured into the portions corresponding to the members thus made hollow by melting of the wax.

In this case, when the sprue, runner, gate and molten metal (which will hereinafter be referred to generically simply as a mold member) cool and solidify before the portion or portions corresponding to the casting cool and solidify, it becomes impossible to supply the portion or portions with molten metal from the mold member, and consequently when the portion or portions solidify, the casting is deformed by shrinkage or shrinkage cavities are produced in the casting because of shrinkage to thereby render it impossible to obtain an intended proper dental casting.

Furthermore, in the case of the dental casting, the casting is small in size, so that unless by centrifugal pressure (pressure applied by a pressure plunger in the case of pressure casting), pouring of molten metal into the mold member was impossible and pressure resistance of the mold member was also required. When pressure resistance of the mold member is not sufficient, the member may break down or may be deformed to thereby exert adverse effects on the substantial supply capability of molten metal.

Furthermore, since the casting is small in size, the sprue, runner, and the like must also be made small, but because cooling and solidifying of the casting is quick, size reduction in a mold member is impossible, with the ultimate result that the mold also cannot but be increased in size. A detailed description will now be given of a conventional mold with reference to a known embodiment thereof.

FIG. 1 is a longitudinal sectional view of a centrifugal casting mold for use in a conventional bridge, the view showing the case wherein three connected teeth having supporting crowns b on either side of a pontic a in the middle are cast.

The pontic a is made of a mass block having thick-walled portion, and supporting crowns b on both sides of the pontic a are thin-walled. Because there is a great difference in thickness between the pontic and the crowns, it is a general practice to cast them as shown by pouring molten metal through three branched gates c. In this case the thin-walled supporting crowns b on both sides are the first, the gate c is the second, the runner d the third, the sprue e the fourth and the thick-walled pontic a is the last in order in which the molten metal is cooled and solidified. As a result, when molten metal in the pontic a is solidified, it shrinks inwardly. On the other hand, since the molten metal in the sprue e, runner d, and gates c has already been solidified, it cannot find its way through them, so that shrinkage cavities and pores are produced in the pontic a. The defective structure mentioned above produces the following adverse effects.

(i) The presence of cavities makes it difficult for the food pieces left in the mouth to be removed from the cavities, which fact is not desirable for oral hygiene;

(ii) The presence of cavities weakens a casting and makes it liable to breakage;

(iii) The presence of cavities hinders bonding of porcelain with a ceramic material in fusing the porcelain over the material and in firing and produces foams, leading to fatal defects;

(iv) The presence of cavities reduces aesthetic value of an article; and (v) The presence of cavities reduces dimensional accuracy because of the deformation brought about by shrinkage.

In consideration of the drawbacks described above, it is a general practice to enlarge mold members such as a sprue, runner in order to delay the solidification of molten metal in the mold members, but the practice has various disadvantages. Namely, when the sprue, runner and gates are enlarged, solidification and shrinkage of the molten metal therein are increased in degree to deform a casting and make it difficult to cut and finish gate portions, and thus reduce dimensional accuracy and also make it necessary to use molten metal for costly dental metals in large quantities.

The sprue varies depending upon the dimensions and volume of a casting, and is usually designed to have a diameter of the order of 2.5 to 5 mm. Particularly, when it is desired to make a thick-walled casting, it is necessary to use a sprue having a separate molten metal reservoir or make a closed molten metal reservoir to feed molten metal from the molten metal reservoir to the shrunk portion of the thick-walled portion to compensate for an amount of shrinkage due to delayed cooling of the thick-walled portion by the use of a sprue having a separate molten metal reservoir or by providing for a closed molten metal reservoir. Thus, the sprue becomes complicated in structure and the use of molten metal must also be increased in quantity.

With respect to a casting different in thickness, recourse is had to quenching caused by a chill effect by using a cooling metal in a portion corresponding to the thick-walled portion, but this is not suitable for precision casting for use in dentistry from the viewpoint of the maintenance of dimensional accuracy.

SUMMARY OF THE INVENTION

Accordingly, a primary object of the invention is to provide a mold member capable of producing a precise dental casting free from the aforesaid disadvantages in a mold for casting metals for dental prosthetic use by delaying the solidification of molten metal in a molding member more than that of molten metal in a mold cavity. Other objects and advantages of the invention will become more apparent from a description thereof that follows in conjunction with the accompanying drawings.

The above object of the invention can be achieved by constructing a mold member of a heat resisting ceramic tubular body.

In preferred embodiments of the invention, a heat insulating layer is formed around the outer periphery of the ceramic tubular body to increase a heat insulating effect.

BRIEF DESCRIPTION OF THE DRAWINGS

In the drawings showing preferred embodiments of the invention wherein:

FIGS. 7 and 10 to 18 are longitudinal sectional views respectively showing various embodiments of the mold member of the invention wherein FIGS. 7 and 10 to 14 are cross-sectional views respectively of basic straight tubular sprues; FIG. 15 shows a sprue having an expanded portion for a molten metal reservoir; FIG. 16 is a cross-sectional view showing an aggregate of a multidivergent sprue, runner and gates; FIG. 17 shows a T-shaped sprue in section; and FIG. 18 shows a closed molten metal reservoir in section.

DETAILED DESCRIPTION OF THE PREFERRED EMBODIMENTS

The mold member of the invention basically comprises a heat resisting ceramic tubular body, and in a further developed form, the member includes a heat insulating layer formed around the outer periphery of the tubular body.

Figure 7:
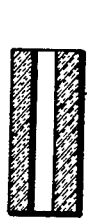
Figure 8:
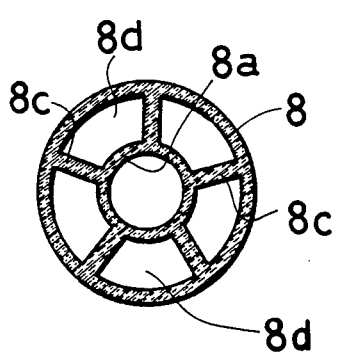
FIGS. 8 and 9 are cross-sectional views showing sprues of a straight beam structure wherein tubular bodies themselves have a heat insulating layer formed around the outer periphery thereof.
Figure 9:
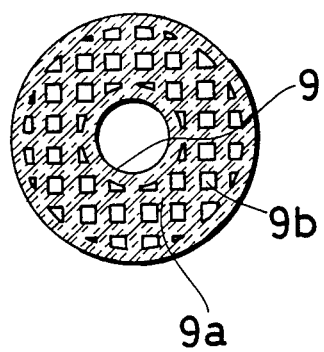
Figure 10:
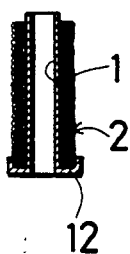

FIGS. 7 to 9 show respectively embodiments of the former type and FIGS. 10 to 18 show those of the latter type, respectively. The fact common to all of the embodiments is the use of heat resisting ceramic which can endure the passage and stay of molten metal for casting. Under the ceramic of the type described above are included alumina ceramic ($Al_2O_3$), silicon nitride type ceramic, zirconia ($ZrO_2.SiO_2$), cordylite ($2MgO.2Al_2O_3.5SiO_2$), mullite ($3Al_2O_3.2SiO_2$), aluminum silicate ($Al_2O_3.SiO_2$) and the like. As the silicon nitride type ceramic is used a sintered body produced by adding sintering assistant such as alumina, magnesium oxide (MgO), yttrium oxide ($Y_2O_3$) to silicon nitride, molding the same, and thereafter subjecting the same to normal pressure sintering or hot press or is also used a sintered body called sialon having aluminum melted in silicon nitride in the form of solid solution. When dental castings are produced by centrifugal casting, thermal shock imparted to a sprue, runner and gate is considerably great. But silicon nitride type ceramic has proved effectively usable for the sprue and the like in that it resists a thermal shock in the range of 400° to 800° C., amounting to two to four times as high as alumina ceramic.

With respect further to tension strength, alumina ceramic is 18 to 38 kg/mm$^2$ in strength, while silicon nitride type ceramic is 40 to 60 kg/mm$^2$, amounting to two to three times higher. Accordingly, alumina ceramic can sufficiently resist the tension imparted to the ceramic when the molten metal shrinks inwardly of the sprue and the like by cooling and solidification. Accordingly, a silicon nitride type ceramic tube is suitable for centrifugal casting and pressure casting which particularly demand pressure resistance of the tube.

Figure 1:
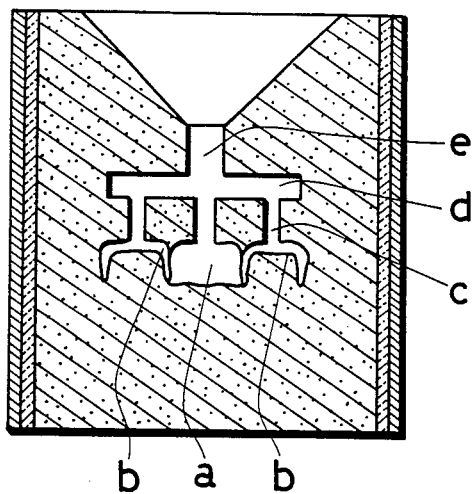
FIG. 1 is a longitudinal sectional view showing one embodiment of a conventional precision casting mold for dental use.

Furthermore, silicon nitride type ceramic is about half as low in thermal conductivity as alumina ceramic and is superior in heat insulating effect and effective for delaying cooling of the sprue and the like. The molds shown in FIGS. 2 to 6 show precision centrifugal casting molds in which a lost-wax process similar to that in FIG. 1 is used as one example, and the materials used are chiefly an Ni-Cr alloy. A detailed description item by item will later be given of the kind, material and structure of a heat insulating layer.

Figure 2:
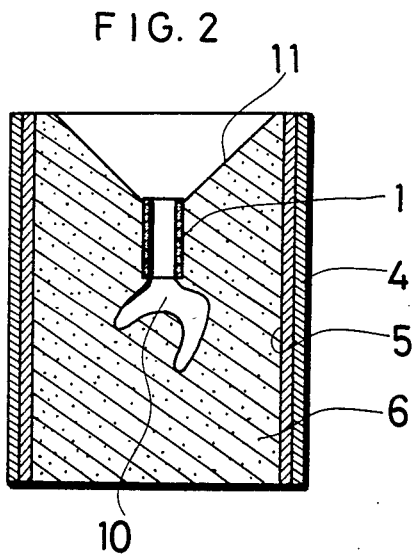
FIGS. 2 to 6 are longitudinal sectional views respectively of molds wherein various mold members of the invention are used.
Figure 3:
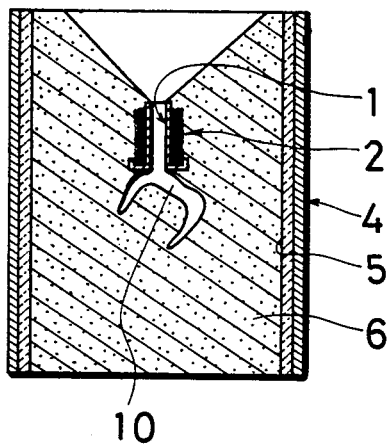
Figure 4:
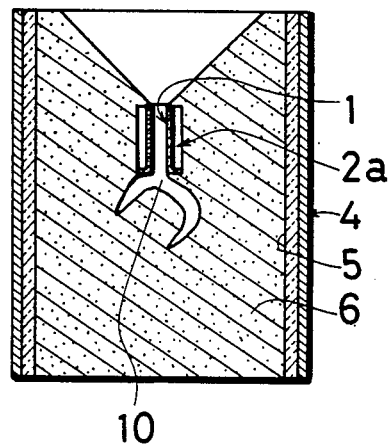
Figure 5:
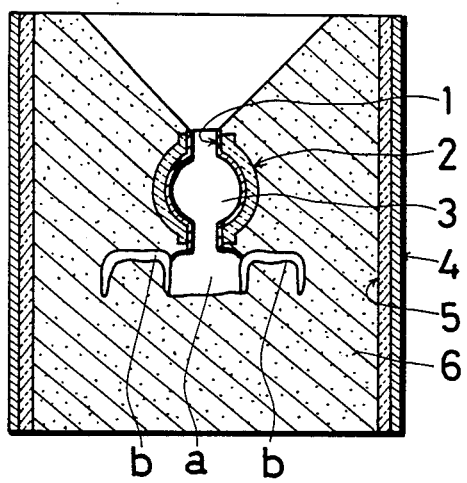

FIG. 7 shows a straight tubular sprue 1 made of the above ceramic, and FIG. 2 shows the state of the sprue 1 set in the mold. As shown, the sprue 1 is set approximately linearly between a pouring cup 11 and a mold cavity 10. The numeral 6 designates an investment; 5 a ring made of a heat resisting material such as asbestos; and 4 designates a mold frame ring. Out of molten metal (not shown) that part of the molten metal staying in the sprue 1 is in direct contact with the investment 6 because ceramic is low in thermal conductivity. The molten metal in the sprue 1 is delayed in cooling and solidification more than that in the cavity 10 and can prevent shrinkage cavities by feeding necessary molten metal from within the sprue 1 to the cavity 10 when the molten metal in the cavity 10 solidifies and can also improve resistance to the pressure of the molten metal.

Instead of dense ceramic, when a ceramic foamed body having a suitable foaming rate (having foamed pores which permit no entry of molten metal thereinto) is used, even if pressure resistance is slightly reduced, the air within the foamed pores is placed under a kind of heat insulating action, so that a heat insulating effect is further increased.

FIGS. 8 to 9 show preferred embodiments of the mold for improving pressure resistance and heat insulation at the same time. The mold in FIG. 8 comprises a hollow tube 8a in the middle, a concentric outer tube 8 disposed outside of the tube 8a, and beam members 8c spanned radially between the tubes 8 and 8a. The air in the spaces 8d between the beam members 8c functions to insulate heat and the pressure resistance of the hollow tube 8a is improved by the beam members 8c and the outer tube 8.

The mold in FIG. 9 comprises a hollow tube 9 in the middle and honeycombed beam members 9a formed in a ringlike manner around the outer periphery of the tube 9, and out of the combination those honeycombed beam members 9a improve heat insulation provided by the air inside the honeycombed spaces 9b by the heat insulating property and pressure resisting strength due to the beam structure. When sprues in FIGS. 8 and 9 are set in the molds, it is desired to prevent an investment and molten metal from penetrating through the interior of the molds by placing blind covers (not shown) on the upper and lower ends of the sprues. The embodiments in FIGS. 7 to 9 are shown in form of a straight tubular sprue, and various forms of sprue may be employed, if necessary. In view of a description to be later given with reference to FIGS. 10 to 18, it is possible to employ the shapes of mold members corresponding to the description, but a description of the shapes are omitted for avoidance of repetition.

FIGS. 10 to 18 show embodiments consisting respectively of a single ceramic tubular body and a material different from the tubular body material or a heat insulating layer disposed around the outer periphery of the tubular body, the heat insulating layer having pores positively formed therein by making the material vanish by burning the same in the mold. FIGS. 10 to 15 show sprues. The sprue in FIG. 10 consists of a heat resisting ceramic sintered body, and is one of the embodiments of a heat insulating layer consisting of a substantially hollow tubular sprue 1 having an outward flange 12 at the lower end and a wound body 2 of heat resisting ceramic fiber such as alumina fiber, zirconia fiber, silicon carbide fiber, the wound body being wound around the outside of the sprue 1. The wound body 2 does not vanish, unlike the case in FIG. 3, by firing even if heated to 800° to 900° C. so as to melt and evaporate wax in the mold, but is left intact in its form and functions to provide insulation between the sprue 1 and an investment 6. Namely, to cite an example, since the heat resisting temperature of the ceramic fiber is in the range of 1400° to 1800° C. at highest, the fiber can sufficiently resist the temperature of molten metal in the range of 1200° to 1300° C. and since the ceramic tubular body 1 has also heat resistance higher than the ceramic fiber, no problem arises as to casting. Because the ceramic fibers have much space between themselves, the fibers are excellent in heat insulating effect.

Figure 11:
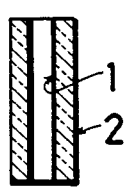

FIG. 11 shows a hollow tubular sprue 1 consisting of a heat insulating layer of a ringlike shaped body 2 of ceramic fiber and heat resisting ceramic slip coating applied around the inner periphery of the layer to a certain thickness and fired.

Figure 12:
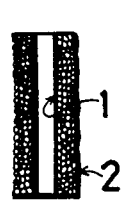

FIG. 12 shows a sprue 1 consisting of a hollow tubular heat resisting ceramic foamed body 2 used as a heat insulating layer and a laminated fired body having ceramic slip coated in the same manner as above over the inner periphery of the heat insulating layer. In the sprues in FIGS. 11 and 12 also, the heat insulating layer 2 is left intact in the mold in the same manner as the sprue in FIG. 10. According to the sprue in FIG. 13, a hollow heat resisting ceramic tube 1 having an outward flange 12 at the lower end includes as a heat insulating layer a wound body 2 of high molecular fiber vanishable by firing, such as acrylic fiber, nylon fiber. The wound body 2 itself has no heat insulating effect, but when the body 2 is placed in the mold shown in FIG. 4 and is heated to melt and evaporate the wax contained in the body, there is formed a cavity 2a in the position corresponding to the body 2. This cavity 2a functions to provide an insulating layer in the mold. A similar attempt is shown made in FIG. 14. On the outer periphery of a heat resisting hollow ceramic tube 1 is formed as a heat insulating layer a wound body 2 consisting of a mixture of high molecular fiber vanishable by firing in a similar manner as above and heat resisting powder granules, and in the mold the high molecular fiber alone vanishes by firing to form pores (not shown) between the remaining heat resisting powder granules. FIGS. 10 to 14 show straight tubular composite sprues, respectively, and FIG. 15 shows a sprue having in the midway thereof an expanded portion 3 for use as a molten metal reservoir. The expanded portion 3 is shown in the form of a bulbous expanded portion, and a tubular body 1 is shown as having ceramic slip formed and fired in layers inside a heat insulating layer 2. The sprue in this case is shown in the state of being used in FIG. 5. When the castings such as a pontic a and right and left supporting crowns b which require a large quantity of molten metal shrink, the sprue in this case can sufficiently feed a necessary quantity of molten metal to prevent the formation of shrinkage cavities because the molten metal is brought into an unsolidified state in the expanded portion.

FIG. 16 shows a mold member adapted for the mold in FIG. 1 and constructed of a ceramic slip laminated fired body 1 and a heat insulating layer 2 which are brought into the shape of a manifold-like body comprising one sprue 1e, a runner 1d communicating on one side with the sprue 1e, and a plurality of divergent gates 1c communicating with the other side of the runner 1d. When the mold member is set in the mold, solidification of molten metal in the sprue 1e, runner 1d, and gates 1c is delayed more than that in the mold cavity, so that the formation of shrinkage cavities is deterred.

The mold member in FIG. 17 is a T-shaped tube member comprising a runner 1d and a gate 1e and is used in various combinations with a straight tubular type mold member when multi-connected teeth are cast.

The mold member in FIG. 18 is a closed molten metal reservoir member formed into a hollow bulbous body constructed of a tubular body 1 and a heat insulating layer 2 and open at the lower end. This mold member is suitable as a molten metal reservoir when a thick-walled portion is cast.

Figure 6:
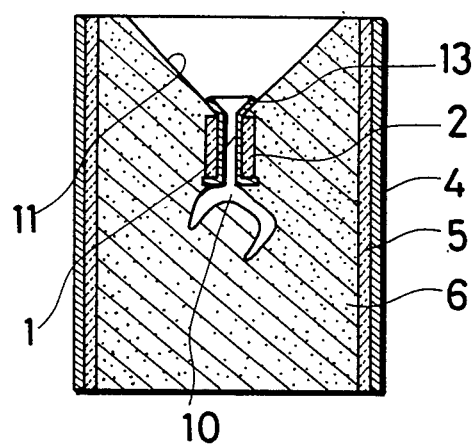
Figure 13:

The sprue in FIG. 6 is a modified sprue of that shown in FIG. 13. Since that portion of a sprue 1 which faces inside an upper pouring cup 11 spreads outwardly, the molten metal in the pouring cup 11 is delayed in solidification because of the heat of the unsolidified molten metal in a divergent portion 13, and for this reason, depressing force against the sprue and other portions succeeding thereto is increased to provide effective casting.

It is to be understood that the dimensions of the composite mold members described above are applicable also to the embodiments (FIGS. 7 to 9) of a single heat resisting ceramic tubular body 1.

The embodiments described above are merely some of the possible embodiments of the invention, and the invention permits the production and utilization of embodiments having various shapes other than those shown such as L-shaped, Y-shaped, cross-shaped, bent tubes, and those different in dimensional percentage.

The invention constructed as above has the following advantages. Since ceramic itself forming a sprue, runner, gate, and a molten metal reservoir is also a nonconductor of heat, it produces a superior heat insulating effect, so that ceramic delays the solidification of molten metal in the mold member more than a casting.

Accordingly, the ceramic mold member makes it possible to obtain a superior casting free of deformation and shrinkage by the use of a sprue and the like smaller in diameter than conventional one. Further, it has been a common practice to provide for a molten metal reservoir about twice as large as that for a quantity of molten metal used in a casting, but the invention makes it possible to serve the purpose by using half of the quantity used for the casting, and depending upon circumstances, it is even possible to go so far as to dispense with a molten metal reservoir.

As a result, the invention generally permits great reduction of the amount of molten metal necessary for casting, and consequently the invention is economically of great advantage in the light of the fact that casting metal for dental prosthetic use is costly.

It also becomes possible to calculate the quantity of molten metal necessary for a casting. The use of the invention makes it possible to reduce in size a pouring cup, sprue, gate and molten metal reservoir, so that not only reduction in the size of a mold is rendered possible but also making of the mold becomes easy.

In addition, in centrifugal casting and even in pressure casting designed to pour casting metal into a mold by a plunger or by application of pressure, pressure resistance is guaranteed because the pouring cup, sprue, gate and molten metal reservoir are made of ceramic.

Since feed efficiency of molten metal is improved also in the case of casting connected teeth in which a pouring cup, sprue, gate and molten metal reservoir are much used, not only the pouring cup, sprue, gate and molten metal reservoir may be less used but also an amount of shrinkage caused by cooling of a thick-walled pontic portion can be compensated by the sprue portion, so that production fissures and shrinkage cavities in the connections of supporting crowns due to inward shrinkage of the pontic can be prevented.

I claim:

1. A mold for use in dental precision casting, said mold comprising a sprue and a dental precision casting mold investment, said investment containing a closed ended cavity in flow communication with said sprue, said sprue comprising a heat resisting ceramic tubular body.

2. A mold according to claim 1 wherein said sprue consists of a tubular body of a heat resisting ceramic foamed body.

3. A mold according to claim 1 wherein said sprue is a straight tubular body.

4. A mold according to claim 1 wherein said sprue comprises inner and outer double hollow tubes and beam members spanned between said two hollow tubes.

5. A mold according to claim 1 wherein said sprue comprises a body having a central cavity and a ringlike honeycombed beam member formed around the outer periphery of said central cavity.

6. A mold according to claim 1 wherein said sprue includes a molten metal reservoir consisting of an outwardly expanded portion in the middle of the tubular body.

7. A mold according to claim 1 further including a pouring cup which spreads outwardly at the top.

8. A mold for use in dental precision casting, said mold substantially constituting in flow communication a pouring cup, a sprue and a gate, and a dental precision casting mold investment, said investment containing a closed ended cavity in flow communication with said gate, the sprue and gate being set in said investment, said sprue consisting of a heat resisting ceramic inner tubular body and a heat insulating layer disposed outside said tubular body and adapted to insulate heat between the tubular body and investment.

9. A mold according to claim 8 wherein said sprue consists of a heat resisting ceramic sintered body and said heat insulating layer consists of a heat resisting ceramic fiber body wound around the outer periphery of said sintered tubular body.

10. A mold according to claim 8 wherein said sprue is made of a fired heat resisting ceramic slip layer and said heat insulating layer is a heat resisting ceramic fiber body wound around the outer periphery of said sprue.

11. A mold according to claim 8 wherein said sprue is a fired body of heat resisting ceramic slip layer and said heat insulating layer is a heat resisting foamed body.

12. A mold according to claim 8 wherein said sprue is made of a heat resisting ceramic sintered body and said heat insulating layer is a body wound around the outer periphery of said sprue, said wound body being made of high molecular fiber vanishable by firing.

13. A mold according to claim 8 wherein said sprue is made of a heat resisting ceramic sintered body and said heat insulating layer is a body wound around the outer periphery of said sprue, said wound body being made of fire resisting power granules and high molecular fiber vanishable by firing.

14. A mold according to claim 8 wherein said tubular body and said heat insulating layer include an outwardly expanded portion in the midway thereof.

15. A mold according to claim 8 wherein said tubular body and said heat insulating layer are straight hollow tubes.

16. A mold according to claim 15 wherein said tubular body is provided at the lower end with an outward flange.

17. A mold according to claim 14 wherein said tubular body and said heat insulating layer include a bulbous expanded portion in the midway of a straight hollow tube.

18. A mold according to claim 8 wherein said tubular body and said heat insulating layer comprise a single sprue, a runner communicating on one side with said sprue, and a plurality of branched gates communicating with the other side of said runner.

19. A mold according to claim 8 wherein said tubular body and said heat insulating layer form a T-shaped tube.

20. A mold according to claim 8 further comprising a molten metal reservoir which consists of a hollow bulb in the sprue open at the lower end.

21. A mold according to any one of claims 1 to 20 wherein said heat resisting ceramic is selected from the group consisting of alumina, silicon nitride, silicon carbide, sialon, zirconia, cordylite, mullite, and aluminum silicate.

22. A mold according to claim 9 wherein said heat resisting ceramic is selected from the group consisting of alumina fiber, zirconia fiber and silicon carbide fiber.

23. A mold according to claim 12 or 13 wherein the high molecular fiber vanishable by firing in said heat insulating layer is selected from acrylic fiber and nylon fiber which form cavities by burning and finish in the process of lost-wax process.

24. A mold according to claims 1 to 20 or 22 wherein the mold is a centrifugal casting mold formed by use of lost-wax process for casting an alloy of Ni-Cr.

25. A device for use in the precision casting of dental prosthetics, the device comprising:
   a container containing investment, the investment having formed therein a closed ended cavity; and
   a sprue in flow communication with the cavity, the sprue comprising a heat resisting body.

26. A device according to claim 25 wherein the sprue consists of a tubular body surrounded by a heat resisting material.

27. A device according to claim 25 wherein the sprue is a straight tube having an inner diameter of the order of 2.5 to 5 millimeters.

28. A device according to claim 26 wherein the sprue is a straight tube having an inner diameter of the order of 2.5 to 5 millimeters.

29. A device according to claim 25 wherein the cavity is formed in the shape of at least a single pontic and at least one crown.

30. A device according to claim 25 whereby the sprue delays solidification of molten metal in the sprue more than that of molten metal in the cavity.

31. A mold for use in dental precision casting comprising:
   a container holding investment, the investment having formed therein a closed ended cavity in the shape of at least a portion of a prosthetic tooth, the cavity formed by use of lost-wax method; and
   a sprue in flow communication with the cavity, the sprue being tubular and having an inner diameter of the order of 2.5 to 5 millimeters, the sprue consisting of silicone nitride ceramic.

* * * * *